United States Patent [19]
Kurpanek

[11] 3,974,854
[45] Aug. 17, 1976

[54] VALVE PARTICULARLY ADAPTED FOR UTILIZATION IN CONTROLLING THE FLOW OF BLOOD

[76] Inventor: Waldemar Helmut Kurpanek, Mercator Str. 3, 4 Duesseldorf 11, Germany

[22] Filed: Jan. 15, 1975

[21] Appl. No.: 541,104

Related U.S. Application Data

[62] Division of Ser. No. 287,062, Sept. 7, 1972, Pat. No. 3,874,002.

[52] U.S. Cl. .............................. 137/512; 137/527; 251/65; 3/1.5; 3/1.7
[51] Int. Cl.² ........................................ F16K 15/03
[58] Field of Search ............. 3/1, 1.5, 1.7; 137/527, 137/512, 527.6; 251/65

[56] References Cited
UNITED STATES PATENTS

| | | | |
|---|---|---|---|
| 2,646,071 | 7/1953 | Wagner | 251/65 X |
| 3,294,115 | 12/1966 | Koenigsberg et al. | 251/65 X |
| 3,370,305 | 2/1968 | Goott et al. | 3/1.5 |
| 3,445,863 | 5/1969 | Wada | 3/1.5 |
| 3,586,029 | 6/1971 | Evers | 137/527 X |

FOREIGN PATENTS OR APPLICATIONS

| | | | |
|---|---|---|---|
| 1,192,521 | 5/1965 | Germany | 251/65 |

Primary Examiner—Ronald L. Frinks
Attorney, Agent, or Firm—Holman & Stern

[57] ABSTRACT

A permanently implantable artificial heart utilizing a pulsatile magneto-motive pump consisting of a pump chamber, which has two cobalt rare-earth permanent magnets spaced apart relative to one another so that unlike poles of each magnet face each other across a predetermined gap, one electromagnet coil, a ferromagnetic piston and a hydraulic fluid. The complete heart consists of two separate half hearts each having one pulsatile magnetic pump, an atrium, a ventricle, respective valves and collapsible hydraulic sacs. A dc pulse applied to the coil determines the pumping stroke rate of the piston which forces hydraulic fluid in and out of the collapsible sacs causing alternating positive and negative pressure gradients in the atrium and ventricle of the heart, thus producing with the help of one directional check valves, a one-directional pulsatile blood flow circulation. The pumping mode of the pistons is designed to act counter directional to each other whereby generated torque forces are greatly neutralized. The total heart is designed to duplicate the natural heart's pumping action by emptying both ventricles simultaneously while the atria are in the process of filling.

4 Claims, 5 Drawing Figures

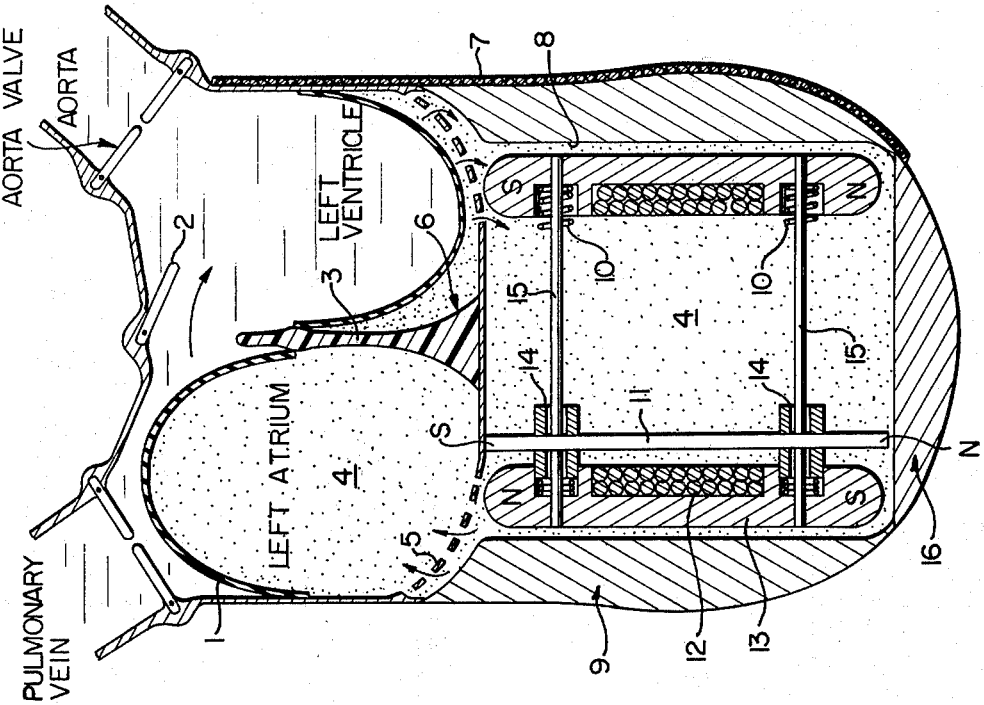
FIG. A1
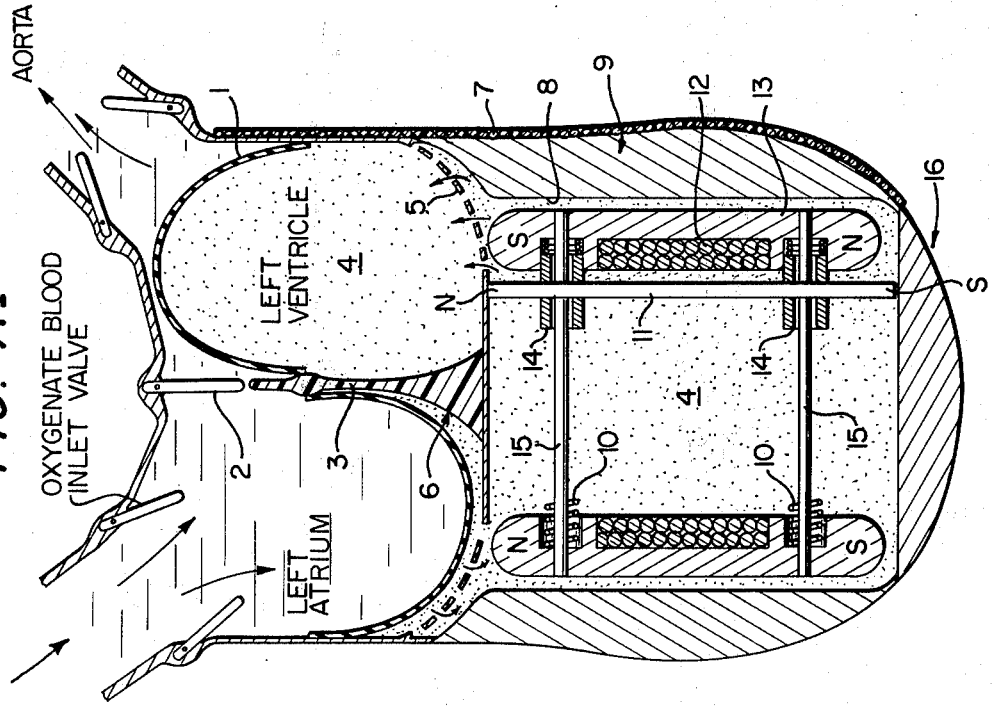
FIG. A2

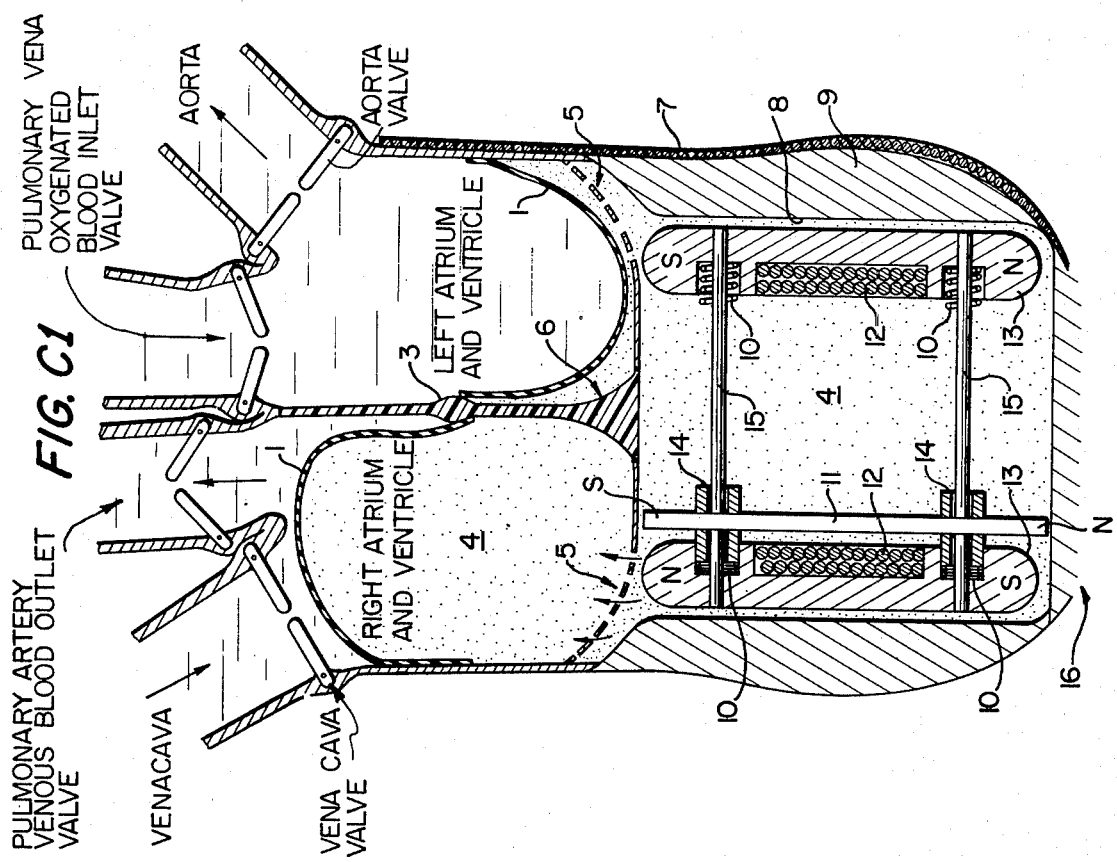
FIG. C1
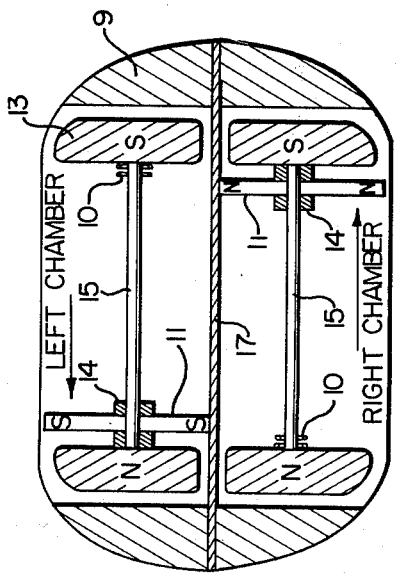
FIG. B1
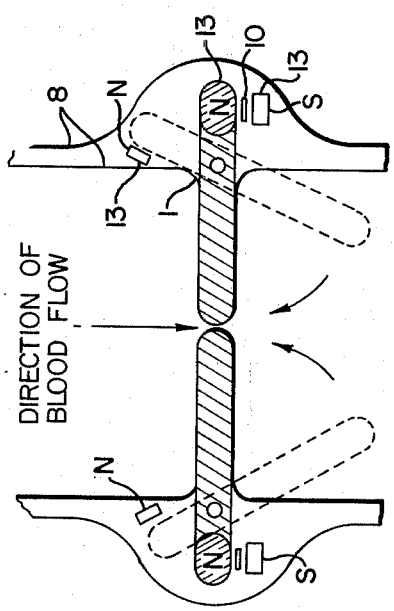
FIG. B2

VALVE PARTICULARLY ADAPTED FOR UTILIZATION IN CONTROLLING THE FLOW OF BLOOD

This is a divisional of application Ser. No. 287,062 filed Sept. 7, 1972, now U.S. Pat. No. 3,874,002.

SUMMARY OF THE INVENTION

The object of this invention is to provide a totally implantable artificial heart having a long lasting, reliable, space saving multipurpose pump, that by virtue of its novel construction serves also as its own motor and valve. The reliability and life expectancy of the magnetic pump is much higher than that of a conventional motor and pump. The magnetic pump functions without reduction gear, brushes, contacts, ballbearings, separate motor, etc., to mention only a few advantages. The magnetic pump is a bistable device staying in the on or off position without a holding current or mechanical holding force thereby functioning additionally as a valve. The pump motor is the pumping piston itself and is the one and only moving part. Upon electric triggering the pump starts immediately with full power. The cobalt rare-earth magnets and the coil are fully encased so that only the piston and the pump's cylinder come in contact with the pumped medium. The magnetic pump functioning without brushes, contacts, etc., and being fully encased can be operated in an explosive or highly inflammable medium as well as in a vacuum with absolute safety. The temperature in which it can be successfully operated ranges from absolute zero $-270°$ to $+750°C$.

The operational durability of the magneto-motive pump depends to a high degree on the magnets used.

Modern magnets of the cobalt with rare-earth element type such as the cobalt samarium magnet which has a resistance to demagnetization that is 20 to 50 times superior to conventional magnets of the Alnico type show great advantages as the following tabulation of properties indicates:

Cobalt Samarium Magnets
Magnetic Properties:
Coersive force = 9,000 Oersted
Intrinsic coersive force = 25,000 Oersted
Residual induction = 9,000 Gauss
Energy product, max. = $20 \times 10^6$ Gauss-Oersted
Curie temperature = 850°C
Temperature coefficient = 0.02% per °C
Physical Properties:
Specific gravity = 8 g/cc
Electric resistivity = $5 \times 10^{-4}$ Ohm-cm
Mechanical Properties:
Tensile strength = 8,000 psi
Compressive strength = 10,000 psi
Flexual strength = 12,000 psi The cobalt samarium magnet has been shown when exposed to a demagnetizing field H of 9000 Oersted to retain its full magnetic strength. In this invention the two magnets are facing with complimentary poles, thereby creating a circular, fully closed ring flux field with a coil set between them producing a mere few hundred Oersted field strength, and opposing only one magnet at a time while at the same time increasing the field strength of the other magnet. The activation of the coil produces a magnetic flux with the highest flux density within the piston. From the poles of the piston the flux enters the opposite poles of the magnet thus continually magnetizing one pole per piston stroke thereby holding the magnets at their magnetic saturation point and preventing possible degradation. A soft iron shield placed between coil and magnets (also 12) permits a flow of magnetic flux on the outside of the coil thus preventing the flux to enter the similarly poled magnet.

Theoretically, should a field H of say 1000 Oersted temporarily demagnetize some magnetic domains, then it would readily be remagnetized as the field of 9000 Oersted plus the field of 1000 Oersted with an energy product of greater than $20 \times 10^6$ Gauss-Oersted again fully closes the circular ring flux field of the two magnets.

In industry the cobalt-samarium magnets are used to focus Travelling Wave Tubes where fields of 9000 Oersted are always opposing.

This should prove beyond doubt that a mere 1000 Oersted field cannot produce a degradation of field strength with time in this application.

In the permanently implantable total artificial heart according to the invention the pump exhibits ideal suitability to closely duplicate the pumping action of a normal heart. Although it may be theorized that a mechanical heart pump must not necessarily have to function as a duplicate of the natural heart pump it does nevertheless solve a lot of problems to adhere respectfully to the modes of the naturally created pumping system.

The pulsatile magneto-motive heart pump has been designed to duplicate the natural pumping modes of an actual heart very closely.

It also consists of two atria and two ventricles of which both ventricles are simultaneously emptied while the atria are in the process of filling.

Moreover a simple but very reliable one-directional valve system has been designed which together produce both the high and the low pressure periods (systolic and diastolic) as found in the natural heart's pumping action, thereby eliminating negative pressure states in both atria due to the suction action of the ventricles as found in designs omitting that principle. The check-valve system is designed to give a natural one-directional pulsatile blood flow circulation and it responds similarly as the natural valve system to an increased blood pressure gradient which overcomes the magnetic force of attraction of the valve flaps thereby opening the valve. A reduction of the blood pressure gradient causes the valve to close and remain closed against an increased blood pressure gradient force in the opposite direction. Thus permitting a one-directional blood flow circulation only. The valve flaps and the elastic diaphragm sacs are constructed not to come in contact with either the chamber walls nor with each other thereby preventing hemolysis.

The atria are designed as large elastic blood reservoirs thus providing for rapid ventricular filling. The large atria are filled by venous pressure without the necessity of applying the negative pressure gradient. The atria are designed to counter any negative pressure gradient by collapsing slightly inward thus preventing the propagation of the negative pressure gradient to the venous system. The complete separation of right and left heart into two independent units reduces the surgical problems considerably. Each separate heart unit is individually controlled, thus permitting a more detailed imitation of the physiologic stroke characteristics.

The pumping mode of the pistons is designed to act counter-directional to each other whereby generated torque forces are greatly neutralized.

The hearts are shown with an induction coil for transmission of electric energy through the patients chest and the battery for storage. Should a superior power source be used such as possibly the plutonium-238 isotope power source then of course there is no need for the coil and batteries.

The hearts are designed to give the wearer a feeling of security and confidence for should a diaphragm (sac) rupture and the hydraulic fluid used be of a nature not harmful to the wearer's system then the normal function of the heart would not be interrupted. The hydraulic fluid would slowly be replaced by the blood and a gradual hemolysis would occur.

By employing a different colour marking fluid in each separate heart unit, say blue in one and green in the other, this would indicate in which heart unit a diaphragm rupture occurred. For the wearer there would be ample time to seek medical aid as with additional blood transfusions many days could be bridged without harmful effects. Unlike gas-driven heart pumps, air embolism cannot occur because there is no gas present.

The primary advantages between the artificial heart using the pump constructed according to this invention and other constructions known from the prior art are simplicity, reliability, compactness and functional life expectancy.

When compared with a natural heart the following characteristics become evident:

| Natural heart | | Magneto-Motive heart |
|---|---|---|
| Circumference | 25 cm | Yes |
| Breadth | 9 cm | Yes |
| Length | 15 cm | Yes |
| Weight | 300 gr | Possible (without batteries, induction coil and hydraulic fluid) |
| Output 5 to 10 litres/min | | Each side - yes |
| Aortic arterial pressure 120–180 mm Hg | | Yes |
| Pulmonary arterial pressure 20–80 mm Hg | | Yes |
| Pump rate 60–120 beats/min | | Yes |
| Diastole 0.5 sec | | Yes |
| Systole 0.3 sec | | Yes |
| Ventricular volume 120 ml | | Yes |

A further embodiment of the invention envisages a heart design which bears such advantages as: one heart unit, less weight, lower power consumption, smaller volume, etc. But as all things in nature it is counterbalanced with the disadvantage namely that it pumps blood alternatingly into the pulmonary circulation and with the next stroke into the main circulatory system. Should this pumping mode not prove detrimental to the human organism then it should possibly be given priority. The embodiments disclosed are limited to two for reasons of brevity, but it should be noted that a number of different heart units may be designed within the scope of the present invention. The pulsatile magneto-motive pump, motor, valve used in the heart system has been successfully tested by the inventor over a period of almost three years. The novel construction of the closed ring flux field that continually magnetizes the permanent magnets and the application of the superior cobalt rare-earth magnets allowed this invention for the first time to become functionally possible.

BRIEF DESCRIPTION OF THE DRAWINGS

A better understanding will be gained of the nature of the instant invention from a study of the following detailed description thereof taken with reference to the attached drawings wherein:

FIGS. A1 and A2 show the Pulsatile Magneto-Motive Pump in action in the left heart of a Permanently Implantable Total Artificial Heart according to one aspect of the invention.

FIG. B1 shows a top view of the two chamber halves pumping counter-directional thereby greatly neutralizing created torque forces.

FIG. B2 shows a magnetic one-directional blood flow valve.

FIG. C1 shows a further embodiment of the invention where one pulsatile magneto-motive pump serving as a complete artificial heart where one heart chamber serves the function of both atrium and ventricle and where a partition, the hearts septum, separates left from right heart.

DETAILED DESCRIPTION OF PREFERRED EMBODIMENTS OF THE INVENTION

The present invention functions due to the use of a novel construction of a magneto-motive pump, which also functions as its own magneto-motive motor and as a magneto-motive valve all these functions being incorporated into one unit to form a permanently implantable total artificial heart. The invention as may be seen from the drawings, includes two cobalt rare-earth permanent magnets 13 set at a distance apart so that the magnetic poles of one magnet face the magnet poles of the other magnet having opposite magnetic polarity thereby forming a closed ring flux field. The two magnets are rigidly mounted into a piston chamber which also serves as a magnetic shield 8. At the magnets midsection an electro magnetic coil 12 encircles the inside of the piston chamber. A ferro-magnetic piston 11 slides between the magnets inside the coil with two guide blocks 14 containing linear bearings on two guiding rods 15. Compression springs 10 check the sliding motion.

A dc pulse is provided which energizes the coil producing magnetic lines of force which are perpendicular to the poles of the permanent magnets. The highest flux density produced by the coil is concentrated within the ferro-magnetic piston whereby the piston becomes magnetically polarized. The piston is thereupon repelled by like poles and attracted by unlike poles of the permanent magnets. This action is reversed by a dc pulse of opposite polarity thus resulting in a reciprocating motion of the piston between the magnetic poles of the magnets respective to the alternating electric pulse frequency.

The reciprocating motor motion of the piston between the magnets 13 is utilised by the introduction of a piston rod thus resulting in the formation of a Reciprocating Magneto-Motive Motor.

The reciprocating motor changes its function to a pump through the introduction of a hydraulic fluid. The piston now pumps hydraulic fluid in the reciprocation mode through the pump chamber.

The introduction of a magnetic one-directional check valve system further results in the development of a one-directional pulsatile pumping action. The piston after completion of a stroke remains in a holding bistable position at the face of the magnets due to the magnetic force of attraction without the necessity of mechanical means or holding current until the subsequent dc pulse is applied.

Additionally the introduction of a seal piston housing, a seal piston contact surface at the magnets face and substituting the piston with a valve sealing piston the pump functions as a Bistable Pulsatile Magneto-Motive Valve.

FIGS. A1 and A2 represent therefore a Permanently Implantable Total Artificial Heart according to the instant invention comprising as two separate units the left and the right heart.

According to one embodiment of the invention each heart unit has a magneto-motive pump, two elastic diaphragm sacs 1, one atrium chamber, one ventricle chamber, three magnetic one-directional valves and the encasing for the heart units. The pump forces hydraulic fluid 4 through two perforated parts of the pump cylinder 5 alternatively against the elastic diaphragm sacs 1 into the atrium and out of the ventricle chamber. The atrium diaphragm sac forces the blood through the magnetic one-directional ventrical inlet valve 2 into the ventricle (FIG. A2). The next stroke fills the atrium through the magnetic one-directional oxygenated blood inlet valve from the pulmonary vein and the ventricle forces the blood through the magnetic one-directional oxygenated blood outlet valve into the aorta (FIG. A1). The stroke characteristic is controlled partition 3 below the ventricle inlet valve and regulated by an electronic circuit 16 at the base of each heart unit. To complete the system an induction coil 7 for the transmission of electrical current through the wearers chest wall and batteries 9 for the storage thereof are included.

FIG. C1 represents in an alternative embodiment of the invention a single heart unit where each chamber functions dually as atrium and ventricle alternatively and being separated completely by a partition, the hearts septum. Four one-directional magnetic valves direct the blood flow. The pump corresponds to that shown in the embodiment according to FIGS. A1 and A2.

FIG. B2 represents a magnetic one-directional blood flow valve. Two valve flaps open under an increased given blood pressure gradient and close due to magnetic attraction when the blood pressure gradient reverses. The valve flaps are plastic and contain a permanent magnet 13 or soft iron piece which is magnetically attracted by a permanent magnet mounted rigidly inside the outer wall. The valve flaps are hinged and prevented from opening in the other direction by a stopper block and concussion spring 10.

The valve flaps and the inner wall are covered by an elastic diaphragm 1 preventing the blood from entering the magnetically shielded compartment.

It should be understood that the present invention is not limited to the embodiments disclosed but to such modifications as reasonably and properly come within its scope and as might be suggested by one skilled in the pertinent art to which the invention relates.

The embodiment of the invention in which an exclusive property or privilege is claimed is defined in the appended claims:

1. A magnetic unidirectional fluid flow valve particularly controlling the flow of blood comprising at least one elongated valve flap constructed of non-magnetic material, said valve flap being hingedly disposed within a conduit for movement under the force of pressure of a fluid medium in said conduit between a first conduit closing position and a second conduit opening position; magnetic means disposed in both said valve flap and said conduit providing a magnetic force therebetween resisting movement of said valve flap from said first position toward said second position and further effecting a return of said valve flap from said second position to said first position upon a drop in the pressure of the fluid medium within said conduit; means for delimiting the travel of said valve flap in both said positions; and wherein an elastic diaphragm means is disposed about said valve flap and the surrounding area of said conduit.

2. A valve as defined in claim 1, wherein two valve flaps are provided, said flaps being hingedly disposed at opposite walls of said conduit so as to be directly opposite one another, said flaps operating in unison within said conduit.

3. A valve as defined in claim 1, wherein said magnetic means include a pair of oppositely polarized magnets which are respectively disposed in the areas of said conduit adjacent to the limits of travel of said valve flap, and a further magnet disposed within said valve flap and polarized so as to be attracted by said magnet within the area of said conduit adjacent said first conduit closing position of said valve flap and to be repelled by said magnet within the area of said conduit delimiting said second conduit opening position.

4. A magnetic unidirectional fluid flow valve particularly controlling the flow of blood, said valve comprising two elongated valve flaps constructed of a plastic material and disposed directly opposite one another within a conduit, each valve flap being hingedly disposed within a conduit for movement in unison under the force of pressure of a fluid medium in said conduit between a first position in which said conduit is substantially closed and a second position in which said conduit is substantially open; each of said valve flaps having a magnetic member imbedded therein; magnetic means disposed in said conduit cooperating with said magnetic member of each said valve flap and providing a magnetic force therebetween resisting movement of each said valve flap from said first position toward said second position and further effecting a return of each said valve flap from said second position to said first position upon a drop in the pressure of the fluid medium within said conduit; and means for delimiting the travel of each said valve flap in both said positions, said delimiting means comprising stopper blocks contacting one end of each flap in each of said first and second positions, a compression spring further being provided in association with said stopper block at said first position of each valve flap.

\* \* \* \* \*